United States Patent

Cornicelli et al.

Patent Number: 6,001,866
Date of Patent: Dec. 14, 1999

[54] METHOD FOR TREATING AND PREVENTING INFLAMMATION AND ATHEROSCLEROSIS

[75] Inventors: Joseph A. Cornicelli, Ann Arbor; Bradley D. Tait, Canton; Bharat K. Trivedi, Farmington Hills, all of Mich.

[73] Assignee: Warner-Lambert Company, Morris Plains, N.J.

[21] Appl. No.: 09/051,002

[22] PCT Filed: Sep. 5, 1996

[86] PCT No.: PCT/US96/14242

§ 371 Date: Mar. 20, 1998

§ 102(e) Date: Mar. 20, 1998

[87] PCT Pub. No.: WO97/12613

PCT Pub. Date: Apr. 10, 1997

[51] Int. Cl.⁶ .......................... A61K 31/40; A61K 31/535; A61K 31/54; A61K 31/38

[52] U.S. Cl. .................. 514/410; 514/224.5; 514/229.2; 514/285; 514/365; 514/394; 514/418; 514/419; 514/448

[58] Field of Search .............................. 514/410

[56] References Cited

U.S. PATENT DOCUMENTS

| | | | |
|---|---|---|---|
| 3,388,133 | 6/1968 | Young et al. | 260/326.9 |
| 3,956,295 | 5/1976 | Biere et al. | 260/247.5 FP |
| 4,123,439 | 10/1978 | Balli et al. | 260/326.5 B |
| 4,132,714 | 1/1979 | Petitpierre | 260/326.5 B |
| 4,238,233 | 12/1980 | Yamada et al. | 75/146 |
| 4,608,390 | 8/1986 | Summers, Jr. | 514/575 |
| 4,623,661 | 11/1986 | Summers, Jr. | 514/575 |
| 4,797,495 | 1/1989 | Bair | 548/420 |
| 4,873,257 | 10/1989 | Mobilio | 514/410 |
| 4,873,258 | 10/1989 | Bair | 514/410 |
| 4,876,246 | 10/1989 | Guindon et al. | 514/80 |
| 4,939,133 | 7/1990 | Connor et al. | 514/166 |
| 4,939,145 | 7/1990 | Lau et al. | 514/224.2 |
| 4,952,597 | 8/1990 | Bair | 514/410 |

FOREIGN PATENT DOCUMENTS

| | | |
|---|---|---|
| 0 150 505 | 8/1985 | European Pat. Off. |
| 0 178 413 | 4/1986 | European Pat. Off. |
| 0 199 153 | 10/1986 | European Pat. Off. |
| 0 248 736 | 12/1987 | European Pat. Off. |
| 0 249 407 | 12/1987 | European Pat. Off. |
| 0 410 834 | 1/1991 | European Pat. Off. |
| 0 419 210 | 3/1991 | European Pat. Off. |
| 0 532 091 | 3/1993 | European Pat. Off. |
| 9603375 A1 | 7/1995 | WIPO |

OTHER PUBLICATIONS

Belkner et al., Oxygenation of lipoproteins, by mammalian lipoxygenases, Eur. J. Biochem, vol. 213 (1993), pp. 251–261.

Yia-Herttuala et al., Gene Express. in Macrophage-rich Human Atherosclerotic Lesions, J. Clin. Inv., vol. 87 (1991) pp. 1146–1152.

P.N. Preston et al., Benzimidazoles & Cong. Tricy. Cmpds., Part 1, Interscience, pp. 149–157 (Year not Available).

Gleason et al., Characterization & inhibition of 15–lipoxygenase in human monocytes: comparison with soybean 15–lipoxygenase, Am. J. Physiology, vol. 268 (1995) ppC1301–C1307.

Harats et al., A Possible Role for 15–Lipoxygenase in Atherogenesis, TCM vol. 5, No. 1(1995)pp.29–36.

Schewe et al., Do 15–lipoxygen. have a comm. biolog. role?Elsevier Sci. Pub.,UK,Oct.(1995) pp.369–373.

Conrad et al., Specific inflammatory cytokines regulate the expression of human monocyte 15–lipoxygenase, Proc. Natl. Acad. Sci. USA, vol. 89 Jan. (1992) pp.217–221.

*Primary Examiner*—Laura L. Stockton
*Attorney, Agent, or Firm*—Charles W. Ashbrook

[57] ABSTRACT

This invention provides a method for treating or preventing inflammation or atherosclerosis in mammals comprising administering an effective amount of a 15-LO inhibitor of Formula I:

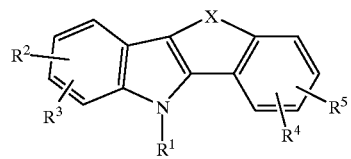

wherein:

$R^1$ is hydrogen or $C_1$–$C_6$ alkyl;

$R^2$, $R^3$, $R^4$, and $R^5$ independently are hydrogen, $C_1$–$C_6$ alkyl, nitro, halo, CN, $OR^6$, $NR^6R^7$, —$CO_2R^6$, $CONR^6R^7$, $CH_2OR^6$, or $CH_2NR^6R^7$, and $R^2$ and $R^3$, and $R^4$ and $R^5$, when attached to adjacent ring atoms, can be —$(CH_2)_{3 \text{ or } 4}$—;

in which $R^6$ and $R^7$ independently are hydrogen, $C_1$–$C_6$ alkyl, phenyl or benzyl, and when taken together with the nitrogen to which they are attached, $R^6$ and $R^7$ can complete a cyclic ring having from 3 to 7 carbon atoms;

X is

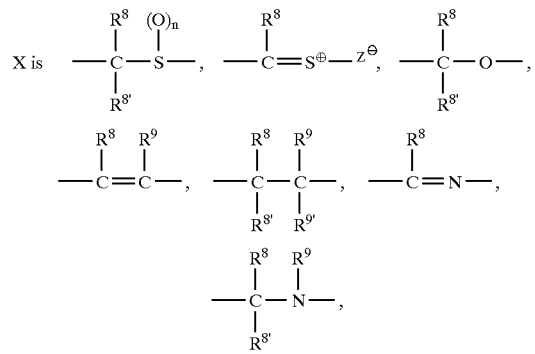

in which $R^8$, $R^{8'}$, $R^9$, and $R^{9'}$ independently are hydrogen or $C_1$–$C_6$ alkyl, n is 0, 1, or 2, and $Z^\ominus$ is an anion, and pharmaceutically acceptable salts thereof.

11 Claims, No Drawings

METHOD FOR TREATING AND PREVENTING INFLAMMATION AND ATHEROSCLEROSIS

This application is a 371 of PCT/US96/14242 filed Sept. 5, 1996.

This invention concerns a method for treating and preventing inflammation or atherosclerosis in mammals by administering a compound which is an inhibitor of the enzyme 15-lipoxygenase (15-LO).

BACKGROUND OF THE INVENTION

Atherosclerosis is a multifactorial disease characterized by excessive intracellular lipid deposition in macrophages, leading to formation of foam cells. The accumulation of lipid-loaded foam cells in the subendothelial space leads to formation of fatty streaks, which are the early atherosclerotic lesions. Oxidative modification of lipids, specifically low-density lipoprotein, has been implicated as a major process in foam-cell formation.

Lipoxygenases are nonheme iron-containing enzymes that catalyze the oxygenation of certain polyunsaturated fatty acids such as lipoproteins. Several different lipoxygenase enzymes are known, each having a characteristic oxidation action. One specific lipoxygenase, namely 15-LO, has been detected in atherosclerotic lesions in mammals, specifically rabbit and man. The enzyme, in addition to its role in oxidative modification of lipoproteins, is important in the inflammatory reaction in the atherosclerotic lesion. Indeed, 15-LO has been shown to be induced in human monocytes by the cytokin IL-4, which is known to be implicated in the inflammatory process.

Another class of lipoxygenase enzymes is 5-lipoxygenase (5-LO). While this enzyme causes oxidation of unsaturated fatty acids, it primarily is responsible for inserting oxygen on position 5 of arachidonic acid. Other lipoxygenases are known; one of the most common and abundant being 12-lipoxygenase (12-LO).

We have now found that inhibitors of 15-LO are especially useful to prevent and treat inflammation and atherosclerosis. While there are several lipoxygenase enzymes, specific inhibition of 15-LO is critical in the inflammatory and atherosclerosis process. All that is required according to this invention is to administer a 15-LO inhibitor, and especially one that is a specific 15-LO inhibitor.

Several classes of organic compounds are 15-LO inhibitors.

Tetracyclic indole and benzopyranoindole compounds are potent 15-LO inhibitors. U.S. Pat. No. 3,388,133 describes benz[b]indolo[2,3-d]-thiopyrano and pyrylium salts as antibacterial and antifungal agents. U.S. Pat. No. 4,132,714 describes a process for making chromenoindoles, which are said to be useful as color-forming agents. U.S. Pat. No. 4,797,495 discloses a wide variety of benzocarbazoles which are said to be antitumor agents. Similarly, benzimidazoles are well known as antiviral agents. U.S. Pat. No. 4,293,558 describes various 1-thiazolinyl-2-aminobenzimidazoles, and U.S. Pat. No. 4,243,813 describes 1-sulfonyl-benzimidazoles. None of those compounds have been described as inhibitors of 15-LO, and none have been utilized in treating inflammation or atherosclerosis. All of these compounds are 15-LO inhibitors and can be employed in the method of this invention.

We have now discovered that compounds which are effective inhibitors of 15-LO are useful in treating and preventing inflammation and atherosclerosis.

SUMMARY OF THE INVENTION

This invention provides a method for treating and preventing inflammation or atherosclerosis in mammals comprising administering an effective amount of a 15-LO inhibitor. The invention preferably employs a specific 15-LO inhibitor. In a preferred embodiment, the 15-LO inhibitor is a benzopyranoindole or related compound as described in U.S. Pat. Nos. 3,388,133, 4,132,714, and 4,797,495, which are incorporated herein by reference. Especially preferred 15-LO inhibitors have Formula I

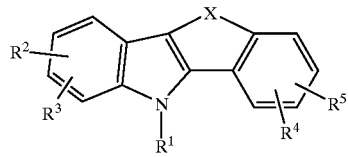

wherein:
$R^1$ is hydrogen or $C_1$–$C_6$ alkyl;
$R^2$, $R^3$, $R^4$, and $R^5$ independently are hydrogen, $C_1$–$C_6$ alkyl, nitro, halo, CN, $OR^6$, $NR^6R^7$, —$CO_2R^6$, $CONR^6R^7$, $CH_2OR^6$, or $CH_2NR^6R^7$, and $R^2$ and $R^3$, and $R^4$ and $R^5$, when attached to adjacent ring atoms, can be —$(CH_2)_{3 \text{ or } 4}$—;
in which $R^6$ and $R^7$ independently are hydrogen, $C_1$–$C_6$ alkyl, phenyl or benzyl, and when taken together with the nitrogen to which they are attached, $R^6$ and $R^7$ can complete a cyclic ring having from 3 to 7 carbon atoms;

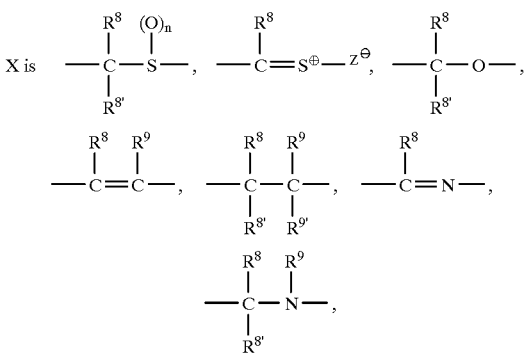

in which $R^8$, $R^{8'}$, $R^9$, and $R^{9'}$ independently are hydrogen or $C_1$–$C_6$ alkyl, n is 0, 1, or 2, and $Z^\ominus$ is an anion, and pharmaceutically acceptable salts thereof.

A preferred method according to this invention employs a compound of the formula

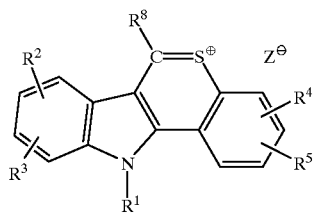

where $R^1$, $R^2$, $R^3$, $R^4$, $R^5$, $R^8$, and $Z^\ominus$ have the above defined meanings. Within this group, preferred compounds to be employed are those wherein $R^1$ is hydrogen, and one or two of $R^2$, $R^3$, $R^4$, and $R^5$ are selected from $C_1$–$C_6$ alkyl, halo, nitro, or $OR^6$, where $R^6$ is preferably $C_1$–$C_6$ alkyl.

Another preferred embodiment utilizes compounds of the formula

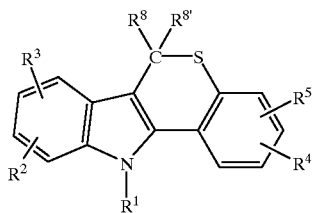

where $R^1$, $R^2$, $R^3$, $R^4$, $R^5$, $R^8$, and $R^{8'}$ are as defined above.

Another preferred method of treatment employs a compound of the formula

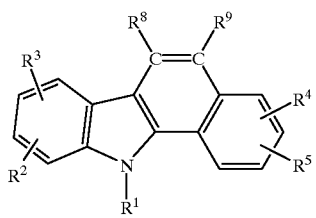

where $R^1$, $R^2$, $R^3$, $R^4$, $R^5$, $R^8$, and $R^9$ are as defined above.

Benzimidazole 15-LO inhibitors to be employed in the method of this invention are known and readily available as described in any of the following United States patents, all of which are incorporated herein by reference: U.S. Pat. Nos. 3,853,908; 3,682,952; 3,850,954; 4,118,742; 4,196,125; 4,216,313; and 4,492,708. Additional benzimidazoles are described in the book entitled *Benzimidazoles and Congeneric Tricyclic Compounds*, P. N. Preston, Ed., John Wiley & Sons, also incorporated herein by reference.

In a preferred embodiment, the 15-LO inhibitor utilized is a benzimidazole having the Formula II

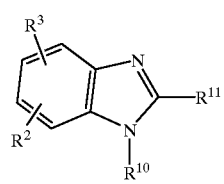

II where $R^2$ and $R^3$ independently are hydrogen, $C_1$–$C_6$ alkyl, nitro, halo, CN, $OR^6$, $NR^6R^7$, —$CO_2R^6$, $CONR^6R^7$, $CH_2OR^6$, or $CH_2NR^6R^7$, and $R^2$ and $R^3$ when attached to adjacent ring atoms can be —$(CH_2)_{3\ or\ 4}$—;

$R^6$ and $R^7$ are as defined above;

$R^{10}$ is $SO_2R^{12}$, hydrogen, $C_1$–$C_6$ alkyl, phenyl, or phenyl substituted with 1, 2, or 3 groups selected from halo, CN, $OR^6$, $C_1$–$C_6$ alkyl, $NR^6R^7$, $CO_2R^6$, $CONR^6R^7$, $CH_2OR^6$, or $CH_2NR^6R^7$; and $R^{11}$ and $R^{12}$ independently are hydrogen, halo, $NR^6R^7$, $OR^6$, $C_1$–$C_6$ alkyl, $C_3$–$C_7$ cycloalkyl optionally containing an O, N, or S atom, phenyl, or phenyl substituted by 1, 2, or 3 groups selected from halo, CN, $OR^6$, $C_1$–$C_6$ alkyl, $NR^6R^7$, —$CO_2R^6$, $CONR^6R^7$, $CH_2OR^6$, or $CH_2NR^6R^7$.

Another preferred method employs a benzimidazole of the formula

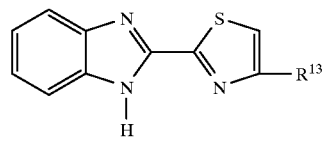

where $R^{13}$ is phenyl, 4-chlorophenyl, 4-fluorophenyl, 4-nitrophenyl, 2,5-dichlorophenyl, 2-furanyl, 2-thienyl, 3-pyridyl, or 4-pyridyl.

In another embodiment, the 15-LO inhibitor utilized is a substituted indole. Typical indoles which can be employed include the carbamates and ureas of Formula III

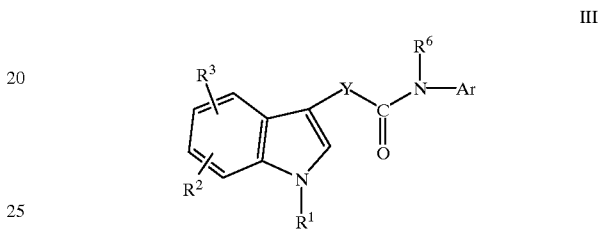

III wherein Y is $CH_2$, S, O, or $NR^7$, and $R^1$, $R^2$, $R^3$, and $R^6$ are as defined above, and Ar is phenyl, Het, and phenyl or Het substituted with 1, 2, or 3 groups selected from halo, CN, $OR^6$, $C_1$–$C_6$ alkyl, $NR^6R^7$, —$CO_2R^6$, $CONR^6R^7$, $CH_2OR^6$, or $CH_2NR^6R^7$, where Het is a heterocyclic group selected from thiophene, furan, pyrrole, isopyrrole, pyrazole, 1,2,3-triazole, 1,2,4-triazole, oxazole, isoxazole, thiazole, isothiazole, 1,2,3-oxadiazole, thiazine, pyridine, pyrazine, piperazine, pyrrolidine, piperidine, and pyridazine, and where Het is optionally substituted with phenyl or substituted phenyl, furanyl, thienyl, or pyridyl, and where $R^6$ and $R^7$ are as defined above. A particularly preferred group of compounds to be employed in the method have the formula

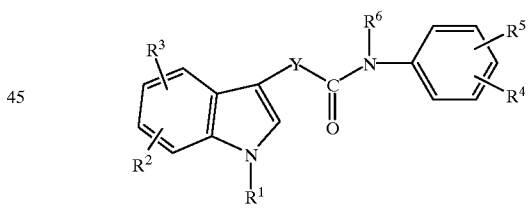

where $R^1$, $R^2$, $R^3$, $R^4$, $R^5$, $R^6$, and Y are as defined above. Such compounds are described in EP 0150505, which is incorporated herein by reference.

Another class of 15-LO inhibitors which can be utilized in the invention are styrenes having the Formula IV

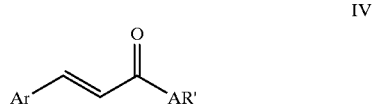

IV wherein Ar and Ar' independently are phenyl, Het, and phenyl or Het substituted with 1, 2, or 3 groups selected from halo, $OR^6$, $C_1$–$C_6$ alkyl, $NR^6R^7$, —$CO_2R^6{}_1$, $CONR^6R^7$, $CH_2OR^6$, and $CH_2NR^6R^7$, where $R^6$ and $R^7$ are as defined above.

A preferred method employs styrene 15-LO inhibitors of the formula

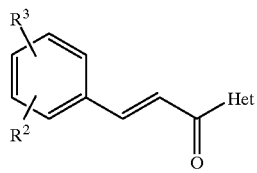

where $R^2$, $R^3$, and Het are as defined above.

Another group of 15-LO inhibitors are catacholes, compounds of the Formula V

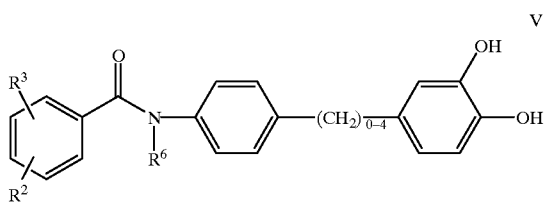

wherein $R^2$, $R^3$, and $R^6$ are as defined above.

Still other 15-LO inhibitors that can be utilized are naphthalenes, especially those of Formula VI

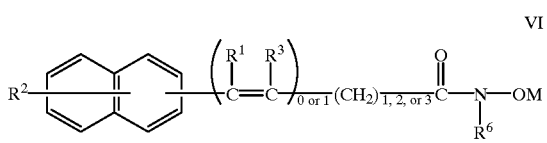

wherein $R^1$, $R^2$, $R^3$, and $R^6$ are as defined above, and M is hydrogen or a cation such as sodium, potassium, or calcium. Such compounds are described in U.S. Pat. No. 4,608,390, incorporated herein by reference.

Another class of 15-LO inhibitors are benzoxadiazines of the general Formula VII

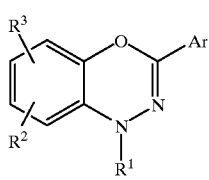

where $R^1$, $R^2$, $R^3$, and Ar are as defined above. Such compounds are described in EP 0410834.

A preferred embodiment utilizes a benzo[a]phenothiazine which is described in U.S. Pat. No. 4,876,246, incorporated herein by reference. Related 15-LO inhibitors that can be employed are phenothiazone derivatives described in U.S. Pat. No. 4,939,145, incorporated herein by reference.

Especially preferred from such classes are compounds having the formulas

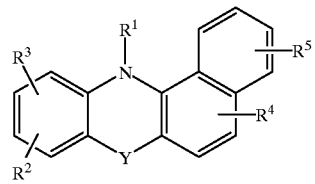

and

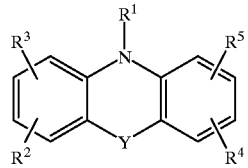

where $R^1$, $R^2$, $R^3$, $R^4$, $R^5$, and Y are as defined above. Such compounds are specifically described in U.S. Pat. Nos. 4,876,246 and 4,939,145.

All that is required to practice the method of this invention is to administer to a mammal a 15-LO inhibiting amount of a 15-LO inhibitor, preferably a specific 15-LO inhibitor.

DETAILED DESCRIPTION OF THE INVENTION

The term "$C_1$–$C_6$ alkyl" means a straight or branched carbon chain such as methyl, ethyl, isopropyl, n-butyl, tert-butyl, sec.-pentyl, 3-methylpentyl, and the like. "Halo" means fluoro, chloro, bromo, and iodo. Ring substituents $R^2$, $R^3$, $R^4$, and $R^5$ can be $OR^6$, where $R^6$ can be hydrogen or $C_1$–$C_6$ alkyl. Typical groups defined by $OR^6$ include hydroxy, methoxy, isopropoxy, tert-butoxy, n-hexyloxy, and the like. Ring substituents also are defined by $NR^6R^7$, which groups include amino, methylamino, diethylamino, N-methyl-N-isohexylamino, and the like. The ring substituents $R^2$, $R^3$, $R^4$, and $R^5$ can also be a carboxylic acid, ester, carboxamide, and methylamino group. Typical esters include methoxycarbonyl and ethoxycarbonyl. Typical carboxamide groups include aminocarbonyl, methylaminocarbonyl and N,N-diethylaminocarbonyl. Typical methylamino groups include methylaminomethyl, ethylaminomethyl, and the like.

The term "$Z^{\ominus}$" in the above formula is an anion such as perchlorate or halide, for instance chloride, bromide, or the like.

The compounds to be employed in the method of this invention are known. They can be prepared by processes described in the art. For example, U.S. Pat. No. 3,388,133, which is incorporated herein by reference, describes reaction of a phenylhydrazine with a thiochroman-4-one to give compounds of Formula I wherein X is

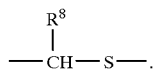

This reaction scheme is applicable to other compounds, for example according to the following scheme

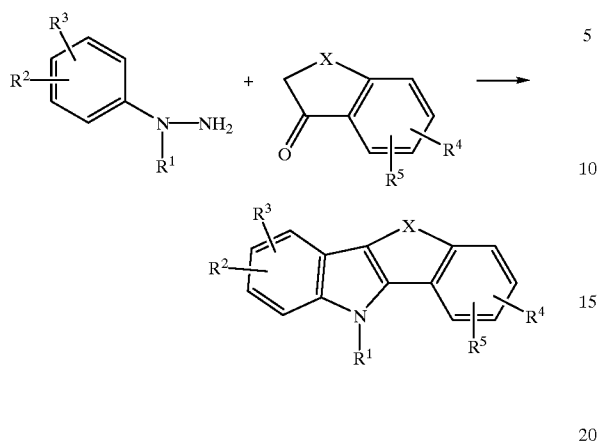

The 15-LO inhibitors are effective for treating inflammation and atherosclerosis. A characteristic feature of atherosclerosis is the accumulation of cholesterol ester engorged from foam cells. Foam cells are derived from circulating monocytes which invade artery walls in response to hypercholesterolemia, and mature into tissue macrophages. The enzyme 15-LO has been implicated in inflammatory disorders and in the origin and recruitment of foam cells (see Harats, et al., *Trends Cardioivasc. Med.,* 1995;5(1):29–36). This enzyme is capable of oxidizing esterified polyenoic fatty acids, such as those found in phospholipids. Treatment of experimental animals with antioxidants which reduce hydroperoxides produced by 15-LO has been shown to retard the progression of atherosclerotic lesions. Accordingly, administering compounds which inhibit 15-LO is an effective way to treat and prevent atherosclerosis.

The compounds described above are effective inhibitors of 15-LO when evaluated in standard assays routinely utilized to measure 15-LO activity. Specifically, representative compounds were evaluated by the methods described by Auerbach, et al., *Analytical Biochemistry,* 1992;201:375–380. Two in vitro assays were utilized, both utilizing rabbit reticulocyte 15-LO, and linoleic acid as substrate, to enzymatically produce a peroxide oxidation product known as 13(S)-HPODE. N-Benzoyl leucomethylene blue was utilized as a calorimetric reagent for detection and quantification of the peroxide formation. Also, HPLC was utilized to quantify the oxidation following incubation at 4° C. for 10 minutes.

The 15-LO inhibitory activity of representative compounds is presented in Table 1. Data Column 1 gives the concentration of compound required to inhibit 50% of the activity of 15-LO ($IC_{50}$) when measured by the HPLC method of Auerbach, et al. Data Column 2 gives the concentration of selected compounds to inhibit 50% of the activity of the 5-LO enzyme.

TABLE 1

Compounds of the Formula

| $R^2$ | $R^3$ | $R^4$ | $R^5$ | $R^8$ | 15-LO $IC_{50}$ $\mu$M | 5-LO |
|---|---|---|---|---|---|---|
| H | H | H | H | H | 1.0–4.0 | |
| H | H | $NO_2$ | H | H | 0.48 | >10 |
| H | H | Cl | H | H | 12.0 | |
| H | H | $CH_3$ | H | H | 1.9 | |
| H | H | H | $CH_3$ | H | 1.0–4.0 | |
| H | H | —$(CH_2)_4$— | | H | 0.5–2.0 | >32 |
| H | $CH_3O$— | H | H | H | 0.70 | >9.6 |
| $CH_3O$ | H | H | H | H | 26.0 | |
| H | H | H | H | $CH_3$ | >25 | |
| H | H | H | H | H | 3.8 | 22 |
| H | H | H | H | H | 1.3 | >100 |
| H | $CH_3O$— | H | H | H | 0.6 | >10 |
| $CH_3O$— | H | H | H | H | 4.5 | >50 |
| H | $CH_3O$— | H | H | H | 4.0 | >50 |
| H | $CH_3O$— | H | H | H | >25 $\mu$m | |

TABLE 1-continued

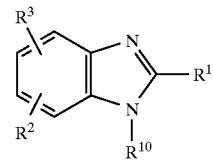

| R² | R³ | R⁸ | R⁴ | R⁵ | 15-LO IC₅₀ |
|---|---|---|---|---|---|
| H | CH₃O— | H | H | H | >25 μM |
| H | H | H | H | H | 1.5 >10 |

As noted above, benzimidazoles are especially preferred 15-LO inhibitors to be employed in the claimed method. The 15-LO inhibitory activity of typical benzimidazoles are given in Table 2.

TABLE 2

Compounds of the Formula

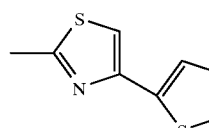

| R² | R³ | R¹⁰ | R¹¹ | 15-LO IC₅₀ μM | 5-LO IC₅₀ μM |
|---|---|---|---|---|---|
| H | H | H | (thiazole-thiophene) | 1.50 | >10 |
| H | 5-Cl | H | (4-Cl-phenyl) | 0.65 | >10 |
| H | 5-Cl | H | (phenyl) | 0.7 | >10 |
| H | 5-Cl | H | (thiacyclohexyl) | 0.24 | >10 |

Styrenes are potent 15-LO inhibitors which can be employed in the present method. Table 3 gives the 15-LO inhibitor of typical styrenes.

TABLE 3

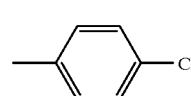

| R² | R³ | Het | 15-LO IC₅₀ μM | 5-LO IC₅₀ μM |
|---|---|---|---|---|
| H | 4-OCH₃ | (2-thienyl) | 1.6 | >10 |

Typical indole 15-LO inhibitors which can be utilized have the activities shown in Table 4.

TABLE 4

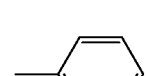

| R₁ | R² | R³ | R⁴ | R⁵ | R⁶ | Y | 15-LO IC₅₀ μM | 5-LO IC₅₀ μM |
|---|---|---|---|---|---|---|---|---|
| H | H | H | H | 3-Cl | H | S | 4 | >10 |
| H | H | H | H | H | H | CH₂ | 1.5 | >10 |

Table 5 gives additional selectivity data for typical 15-LO inhibitors which can be utilized in the method of this invention.

TABLE 5

| | 15-LO IC₅₀ μM | 5-LO IC₅₀ μM |
|---|---|---|
| 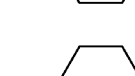 | 2.0 | >30 |
| (benzo-carbazole) | 1.5 | >10 |
| CH₃(CH₂)₃(CH₂—C≡C—)₄(CH₂)₃—COOH | 0.75 | >10 |

As further evidence of 15-LO inhibitors being effective to prevent and treat inflammation and atherosclerosis in animals, one representative compound has been extensively evaluated in cholesterol-fed rabbits over a 12-week period. The compound evaluated "Compound A" was 6,11-dihydro[1]benzothiopyran[4,3-6]-indole, the compound of Formula I where $R^1$, $R^2$, $R^3$, $R^4$, and $R^5$ each are hydrogen, and X is —CH$_2$—S—, i.e.,

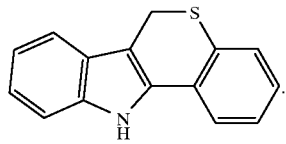

Specific pathogen-free New Zealand White rabbits (≈2.5 kg) were obtained from Myrtle's Rabbitry (Thompson Station, Tenn.). The animals were fed a standard laboratory diet (Ralston Purina, St. Louis, Mo.) and were allowed to become acclimatized for 7 days before initiation of the study, at which time two groups of rabbits (n=10 each) were begun on a diet enriched with cholesterol (0.25% wt/wt), peanut oil (3% wt/wt), and coconut oil (3% wt/wt), with a small amount of applesauce mixed into the food to enhance palatability. This diet was designed to produce a modest hypercholesterolemic response. The control group received no additional treatment. The drug-treated group received 350 mg of Compound A per kilogram body weight per day in their food. Rabbits were permitted access to 40 g of food at ≈12 hour intervals via automated feeders, and diet intake was monitored every day such that the animals received 175 mg/kg/bid. Water was available ad libitum. Body weights were measured at regular intervals throughout the 12-week study. Blood samples were obtained at the indicated intervals for determination of hematocrit and plasma lipid concentrations.

Characterization of Atherosclerotic Lesions

Rabbits were euthanized by an overdose of sodium pentobarbital (150 mg/kg$^{-1}$) and exsanguinated via the abdominal aorta. Aortas were removed from the valve to the ileal bifurcation, opened to expose the intima, and photographed with a Polaroid camera. By use of these photographs, the areas of grossly discernible atherosclerosis were manually integrated on a digitizing pad and calculated with SigmaScan (Jandel Scientific). Aortas were visually subdivided into three areas: arch (aortic valve to first intercostal), thoracic aorta (first intercostal to diaphragm area), and abdominal aorta (diaphragm to ileal bifurcation). In addition to extracting aortas, body tissues were surveyed for indications of adverse reactions.

Determination of Cholesterol Esters and Unesterified Cholesterol Content

Weighed segments of each aortic region (arch, thoracic, and abdominal) were extracted. Esterified and unesterified cholesterol content of aortic tissue were determined by gas chromatography using 5-α-cholestane as an internal standard.

In the control group, the arch area of aortic sections demonstrated about 15% lesion coverage of intima, whereas those animals receiving Compound A showed no lesion coverage. No detectable lesions were seen in either group in the thoracic region. In the abdominal region, the control group exhibited 5% lesion coverage, whereas the treated group exhibited about 1%. The treated group had no detectable cholesterol esters present in the arch, thoracic, or abdominal regions, whereas the control group had about 2 mg/g tissue wet weight of cholesterol esters in the arch region, none in the thoracic region, and about 0.6 mg/g in the abdominal region. Test animals and the control group had about the same amount of unesterified cholesterol in the thoracic and abdominal regions (0.7–0.8 mg/g tissue wet weight), while in the arch region, the control group had about 1.4 mg/g while the treated group had about 0.8 mg/g.

These data establish that administration of a 15-LO inhibitor effectively protects against the development of atherosclerosis in animals.

In an especially preferred embodiment of this invention, the 15-LO inhibitor utilized is a specific inhibitor of 15-LO. The term "specific" as used herein means that a compound inhibits 15-LO at least about ten-fold (10×) more effectively than it inhibits 5-LO. For example, a preferred group of compounds to be employed in the present method are defined by Formula I. A typical compound from within that group is 6,11-dihydro[1]benzothiopyrano[4,3-b]-indole (Compound A). Its 15-LO inhibitory activity is an IC$_{50}$ of 1.3 μM, and its 5-LO inhibitory activity is >100 μM. The compound thus inhibits 15-LO at least about 100 times more potently than it inhibits 5-LO. The compound is therefore a "specific" 15-LO inhibitor for purposes of this invention.

Similarly, a preferred benzimidazole to be employed in the invention is 2-(4-chlorophenyl)-5-chlorobenzimidazole. It has a 15-LO IC$_{50}$ of 0.65 μM, and a 5-LO IC$_{50}$ of greater than 10 μM. Accordingly, its 15-LO to 5-LO ratio of activities is greater than 10, thus making the compound a specific 15-LO inhibitor according to this invention.

All that is required to practice this invention is to administer to a mammal an effective amount of any compound that is a 15-LO inhibitor. For example, the compounds of Formula I are useful for treating atherosclerosis and inflammation by virtue of their ability to inhibit 15-LO as established by the data in Table 1. Accordingly, any compound that is determined to inhibit 15-LO in a test system, such as described above, can be employed in this invention.

For use according to this invention, the compounds can be formulated into compositions suitable for administering to animals, including humans, for treating and preventing inflammation and atherosclerosis. The compounds can be formulated for administration by any route, for instance orally, parenterally, topically, and rectally. For oral administration, for example, a 15-LO inhibitor can be mixed with an inert diluent or with an assimilable edible carrier, or it may be enclosed in a hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations may, of course, be varied and may conveniently be between about 5% to about 80% of the weight of the unit. The amount of active compound in such therapeutically useful compositions is such that a therapeutically effective dosage will be obtained. Preferred compositions or preparations according to the present invention are prepared so that an oral dosage unit form contains between about 5 and 1000 mg of active compound, and ideally about 25 to about 750 mg.

The tablets, troches, pills, capsules, and the like may also contain common pharmaceutical excipients such as binders, sweeteners, and the like. Typical binders include gum tragacanth, acacia, corn starch, and gelatin, as well as excipients such as dicalcium phosphate. Typical disintegrating agents include corn starch, potato starch, alginic acid, and the like. A commonly used lubricant is magnesium stearate. Typical sweetening agents are sucrose, lactose, or saccharin, and flavoring agents such as peppermint, oil of wintergreen, or cherry flavoring can be utilized. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. A syrup or elixir may contain the active compound, sucrose as a sweetening agent, methyl and propylparabens as preservatives, a dye, and flavoring such as cherry or orange flavor. Of course, any material used in preparing any dosage unit form should be pharmaceutically pure and substantially nontoxic in the amounts employed.

The 15-LO inhibitors can also be formulated for topical administration, for instance as patches, salves, creams, ointments, and the like. Agents commonly utilized to enhance transdermal passage can also be employed. The compounds can also be formulated with waxes and the like for convenient rectal administration.

The active 15-LO inhibitor may also be administered parenterally or intraperitoneally. Dispersions can also be prepared in glycerol, liquid polyethylene glycols, and mixtures thereof and in oils. Under ordinary conditions of storage and use, these preparations may contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, a polyol (for example, glycerol, propylene glycol, and liquid polyethylene glycol, and the like), suitable mixtures thereof, and vegetable oils. The proper fluidity can be maintained, for example, by the use of a coating such as lecithin; by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

As used herein, "pharmaceutically acceptable carrier" includes any and all solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the dosage unit forms are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically acceptable carrier in dosage unit form as hereinbefore disclosed. The term "effective amount" means that quantity of a 15-LO inhibitor which has a positive therapeutic effect for treating or preventing the inflammation or the atherosclerosis which affects the mammal. Such amount is that which inhibits the 15-LO enzyme; in other words, a 15-LO inhibiting amount. A unit dosage form can, for example, contain the principal active compound in amounts ranging from about 5 to about 1000 mg, with from about 25 to about 750 mg being preferred. A typical dose will be about 50 to about 500 mg. In the case of compositions containing supplementary active ingredients, the dosages are determined by reference to the usual dose and manner of administration of the said ingredients. The unit dosages typically will be administered from one to four times per day, or as otherwise needed to effect treatment of the disease state.

The invention therefore is a method for treating and preventing inflammation and atherosclerosis in mammals. The compounds are effective in inhibiting the activity of 15-LO, and as such can be administered to a mammal, including a human, to effectively diminish and treat atherosclerosis and inflammation. The compounds will be administered at a dose which is effective to treat atherosclerosis, typically from about 1.0 to about 100 mg/kg of body weight of the subject being treated.

The compounds also are useful for treating and preventing inflammation, for example, swelling due to injuries, swelling around bones and joints, and the like. The compounds will be administered to an animal suffering from inflammation in an anti-inflammatory effective amount that is effective to treat the inflammation. Typical doses will be from about 1.0 to about 100 mg/kg of body weight.

We claim:

1. A method for treating or preventing inflammation or atherosclerosis in a mammal comprising administering a 15-LO inhibiting amount of a compound of Formula I

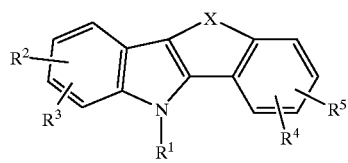

I wherein:

$R^1$ is hydrogen or $C_1$–$C_6$ alkyl;

$R^2$, $R^3$, $R^4$, and $R^5$ independently are hydrogen, $C_1$–$C_6$ alkyl, nitro, halo, CN, $OR^6$, $NR^6R^7$, —$CO_2R^6$, $CONR^6R^7$, $CH_2OR^6$, or —$CH_2NR^6R^7$, or $R^2$ and $R^3$, and $R^4$ and $R^5$, when attached to adjacent ring atoms, can be —$(CH_2)_3$ or —$(CH_2)_4$;

in which $R^6$ and $R^7$ independently are hydrogen, $C_1$–$C_6$ alkyl, phenyl, or benzyl, or when taken together with the nitrogen to which they are attached, $R^6$ and $R^7$ can complete a cyclic ring having from 3 to 7 carbon atoms;

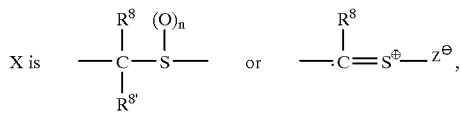

in which $R^8$ and $R^{8'}$ independently are hydrogen or $C_1$–$C_6$ alkyl, n is 0, 1, or 2, and $Z^{\ominus}$ is an anion, or a pharmaceutically acceptable salt thereof.

2. A method according to claim 1 employing a compound of the formula

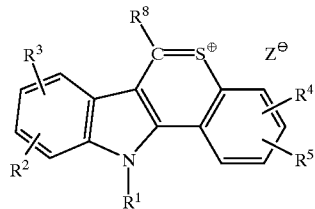

wherein $R^1$, $R^2$, $R^3$, $R^4$, $R^5$, $R^8$, and $Z^{\ominus}$ are as defined above.

3. A method of claim 2 employing a compound wherein $Z^{\ominus}$ is $ClO_4^{\ominus}$ or halo.

4. A method of claim 3 employing a compound wherein $R^8$ is hydrogen.

5. A method of claim 4 employing a compound wherein $R^2$ and $R^3$ both are hydrogen.

6. A method of claim 5 employing a compound wherein $R^5$ is hydrogen.

7. The method of claim 6 employing a compound wherein $R^4$ is $NO_2$.

8. The method of claim 6 employing a compound wherein $R^4$ is $CH_3$.

9. A method of claim 2 employing a compound wherein $R^2$, $R^4$, and $R^5$ are hydrogen and $R^3$ is $CH_3O$—.

10. A method according to claim 1 employing a compound having the formula

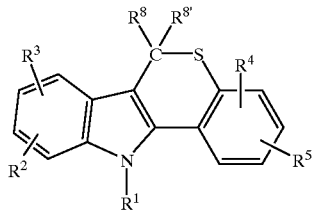

wherein $R^1$, $R^2$, $R^3$, $R^4$, $R^5$, and $R^8$ are as defined above.

11. A method according to claim 10 employing a compound wherein $R^1$, $R^4$, $R^5$, and $R^8$ are hydrogen, $R^2$ and $R^3$ independently are hydrogen or $CH_3O$—.

* * * * *

UNITED STATES PATENT AND TRADEMARK OFFICE
CERTIFICATE OF CORRECTION

PATENT NO. : 6,001,866
DATED : Dec. 14, 1999
INVENTOR(S) : Cornicelli et al.

It is certified that error appears in the above-identified patent and that said Letters Patent is hereby corrected as shown below:

On the face of the Patent insert -- Related U.S. Patent Application Data Section [60] Provisional Application no. 60/005,201, October 5, 1995. --

Column 1, line 6, insert -- which claims priority to U.S. Provisional 60/005,201, filed October 5, 1995. --

Signed and Sealed this

Twelfth Day of September, 2000

Attest:

Q. TODD DICKINSON

*Attesting Officer*           *Director of Patents and Trademarks*